US012570943B2

(12) United States Patent　(10) Patent No.: US 12,570,943 B2
Curtis　(45) Date of Patent: *Mar. 10, 2026

(54) TRICKLE-FILM BIOREACTOR AND METHODS OF USE THEREOF

(71) Applicant: Wayne Rodger Curtis, State College, PA (US)

(72) Inventor: Wayne Rodger Curtis, State College, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/518,199

(22) Filed: Nov. 22, 2023

(65) Prior Publication Data

US 2024/0101947 A1　Mar. 28, 2024

Related U.S. Application Data

(63) Continuation of application No. 16/238,941, filed on Jan. 3, 2019, now Pat. No. 11,873,473, which is a continuation of application No. 14/729,692, filed on Jun. 3, 2015, now Pat. No. 10,208,278, which is a continuation of application No. 12/387,140, filed on Apr. 28, 2009, now abandoned.

(60) Provisional application No. 61/048,327, filed on Apr. 28, 2008.

(51) Int. Cl.
*C12M 1/00* (2006.01)
*C12M 1/12* (2006.01)

(52) U.S. Cl.
CPC ........... *C12M 31/10* (2013.01); *C12M 21/02* (2013.01); *C12M 25/00* (2013.01); *C12M 29/06* (2013.01)

(58) Field of Classification Search
CPC .................................................. C12M 21/02
See application file for complete search history.

(56) References Cited

U.S. PATENT DOCUMENTS

| | | | |
|---|---|---|---|
| 4,966,704 A | 10/1990 | Särner | |
| 4,994,391 A | 2/1991 | Hoffman | |
| 5,151,347 A * | 9/1992 | Delente ................. | C12M 29/24 |
| | | | 435/813 |
| 5,585,266 A | 12/1996 | Plitt et al. | |
| 5,659,977 A | 8/1997 | Jensen et al. | |
| 6,245,555 B1 | 6/2001 | Curtis | |
| 6,416,993 B1 | 7/2002 | Wexler et al. | |
| 6,489,156 B1 | 12/2002 | DiSpirito et al. | |
| 6,667,171 B2 | 12/2003 | Bayless et al. | |
| 6,740,526 B1 | 5/2004 | Curtis | |
| 8,367,379 B2 | 2/2013 | Aikens et al. | |
| 2001/0031491 A1 | 10/2001 | Curtis | |
| 2005/0260553 A1 | 11/2005 | Berzin | |
| 2009/0181434 A1 | 7/2009 | Aikens et al. | |
| 2013/0115689 A1 | 5/2013 | Aikens et al. | |

OTHER PUBLICATIONS

Carvalho et al., "Microalgal Reactors: A Review of Enclosed System Designs and Performances", Biotechnol. Prog. 2006, vol. 22—pp. 1490-1506.

(Continued)

*Primary Examiner* — Jonathan M Hurst
(74) *Attorney, Agent, or Firm* — Buchanan Ingersoll & Rooney PC

(57) ABSTRACT

An apparatus for culturing suspended photosynthetic organisms, specifically a flowing thin film photobioreactor, wherein the flowing thin film photobioreactor comprises a light source and a trickle-film insert comprising screen material.

17 Claims, 9 Drawing Sheets

(56)                References Cited

OTHER PUBLICATIONS

Gamborg et al., "Nutrient Requirements of Suspension Cultures of Soybean Root Cells", Experimental Cell Research, 1968, vol. 50—pp. 151-158 (Abstract Only) 2019.

Grima et al., "Scale-up of Tubular Photobioreactors", Journal of Applied Phycology, 2000, vol. 12—pp. 355-368.

Grobbelaar, "The Influence of Light/Dark Cycles in Mixed Algal Cultures on their Productivity", Bioresource Technology, 1991, vol. 38—pp. 189-194.

Hu et al., "Ultrahigh-cell-density Culture of a Marine Green Alga *Chlorococcum littorale* in a Flat-plate Photobioreactor", Appl. Microbiol. Biotechnol. (1998) vol. 49—pp. 655-662.

Hunter et al., "Purple Phototrophic Bacteria", Advances in Photosynthesis & Respiration, vol. 28 (Abstract Only).

Metzger et al., "Alkadiene and Botryococcene-producing Races of Wild Strains of Botryococcus Braunii", Phytochemistry, 1965, vol. 24, Issue 10—pp. 2305-2312. (Abstract Only).

Miyamoto et al., "Vertical Tubular Reactor for Microalgae Cultivation", Biotechnology Letters, 1988, vol. 10, No. 10—pp. 703-708.

Morita et al., "Photosynthetic Productivity of Conical Helical Tubular Photobioreactor Incorporating Chlorella Sorokiniana Under Field Conditions", Biotechnology & Bioengineering, 2002, vol. 77, No. 2—pp. 155-162.

Murashige et al., "A Revised Medium for Rapid Growth and Bioassays with Tobacco Cultures", Physiolgia Plantarum, 15—pp. 473-497.

Olaizola, "Commercial Production of Astaxanthin from Haemotococcus Pluvialis using 25,000-liter Outdoor Photobioreators", Journal of Applied Phycology, Dec. 2000—pp. 499-506.

Pulz et al., "Photobioreactors: Design and Performance with Respect to Light Energy Input", Advances in Biochemical Engineering/Biotechnology, 1998, vol. 59—pp. 123-152.

Sarramegna et al., "Heterologous Expression of G-protein-coupled Receptors: Comparison of Expression Systems from the Standpoint of Large-scale Production and Purification", Cellular and Molecular Life Sciences CMLS, Aug. 2003, vol. 60, Issue 8—pp. 1529-1546. (Abstract Only).

Tredici et al., "Photobioreactors", Encyclopedia of Industrial Biotechnology: Bioprocess, Bioseparation and Cell Technology, John Wiley & Sons, 2010—pp. 1-18.

Weissman et al., "Photobioreactor Design: Mixing, Carbon Utilization, and Oxygen Accumulation", Biotechnology & Bioengineering, 1988, vol. 31—pp. 336-344.

Wu et al., "Simulation of Algae Growth in a Bench-scale Bubble Column Reactor", Biotechnology & Bioengineering, Oct. 20, 2002, vol. 80, No. 2—13 pages.

Wu et al., "Simulation of Algae Growth in a Bench-scale Internal Loop Airlift Reactor", Chemical Engineering Science, 59, 2004—pp. 2899-2912.

Zhang et al., "Evaluation of a Vertical Flat-plate Photobioreactor for Outdoor Biomass Production and Carbon Dioxide Bio-fixation: Effects of Reactor Dimensions, Irradiation and Cell Concentration on the Biomass Productivity and Irradiation Efficiency", Appl. Microbiol. Biotechnol., 2001, 55—pp. 428-433.

* cited by examiner

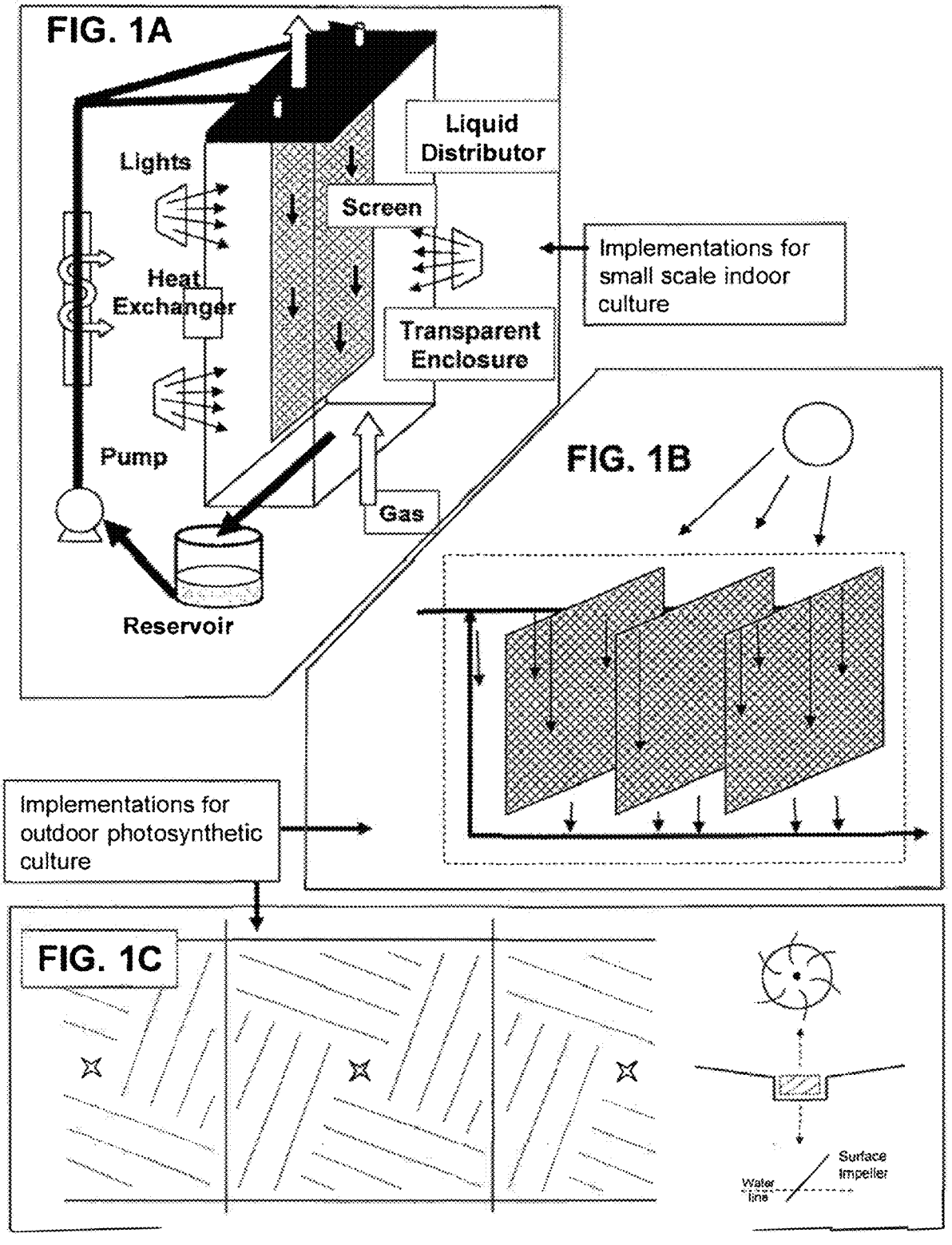

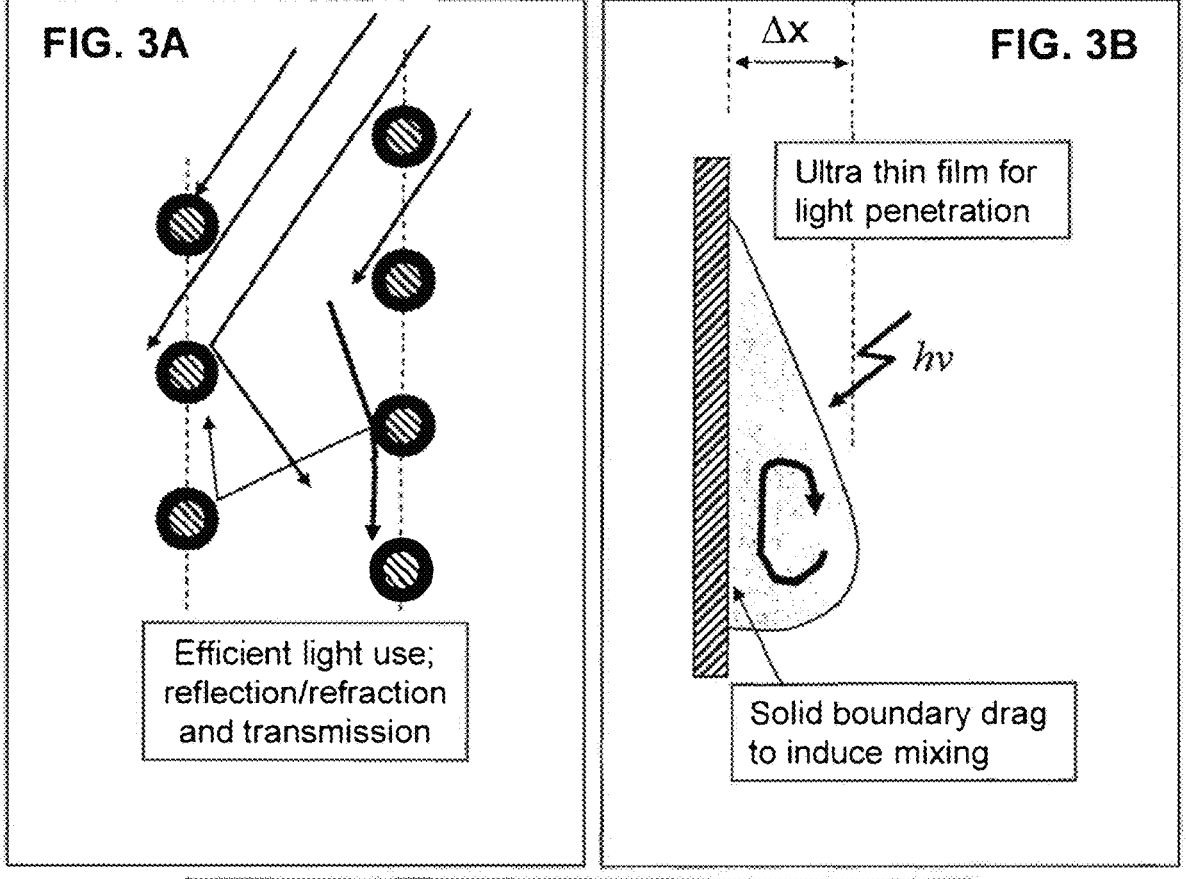
FIG. 3A
Efficient light use; reflection/refraction and transmission
FIG. 3B
$\Delta x$
Ultra thin film for light penetration
$h\nu$
Solid boundary drag to induce mixing
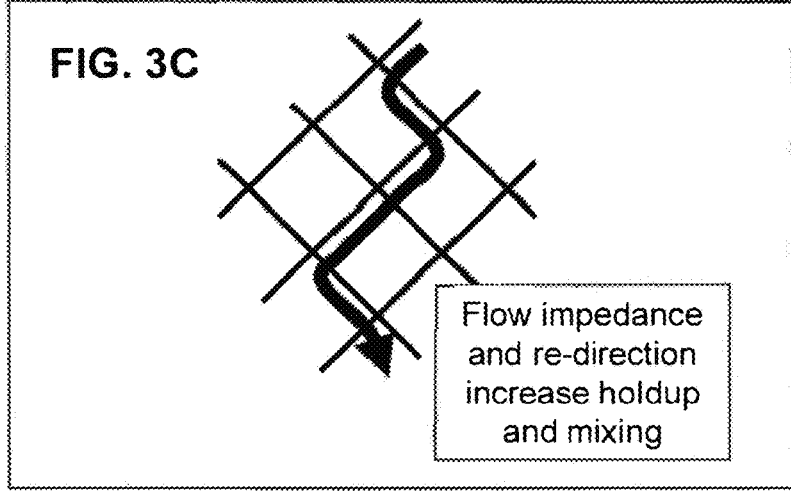
FIG. 3C
Flow impedance and re-direction increase holdup and mixing Hanger support

4B

Stanchion support

4B

Alternative Screen
Cross-sections

Simple
Screen

Crimped
Screen

Screen w/
Spacers

Common characteristic of
screen is minimizing material
and light obstruction and
maintaining 'plug flow' of liquid
and cells.

FIG. 5A

Feed-forward control based on maintaining excess nitrogen and feeding succinate to maintain pH and minimize salt accumulation.

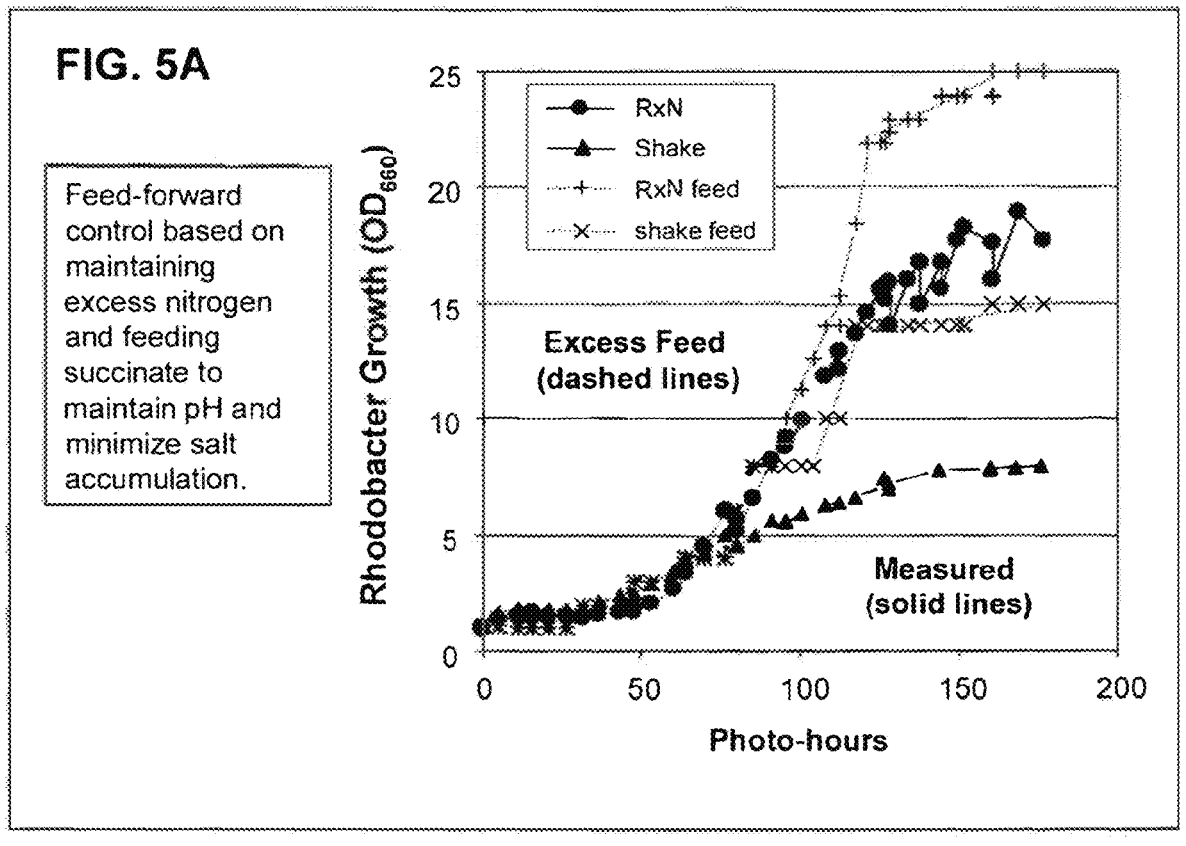

FIG. 5B

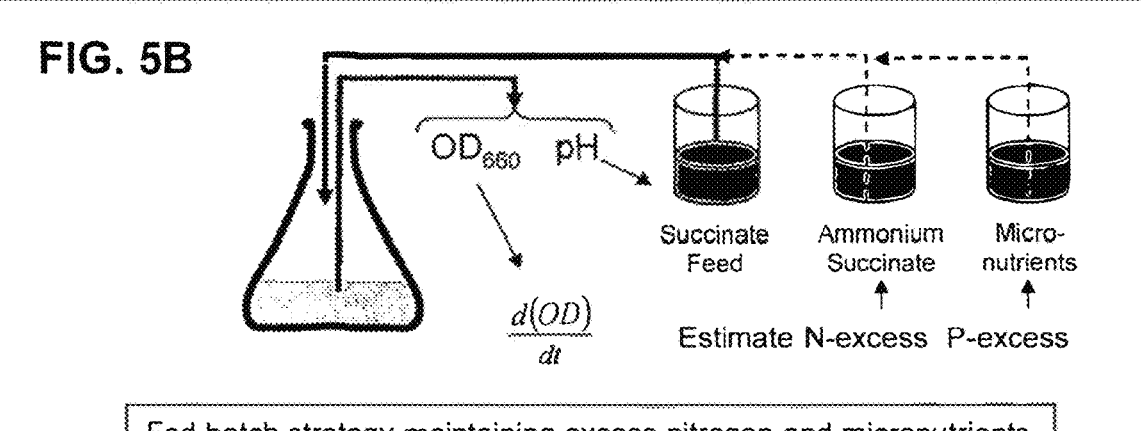

Fed batch strategy maintaining excess nitrogen and micronutrients based on feed forward predictions of growth; carbon balance can be implemented automated feedback control (pH addition of organic acid) or also based on feed-forward stoichiometry.

Stoichimetrically balanced media and correlated ($OD_{550}$) feed strategy facilitates long term continuous culture Feed strategy based on calculated mass of nutrients removed based on correlation with optical density and periodic dry weight correction.

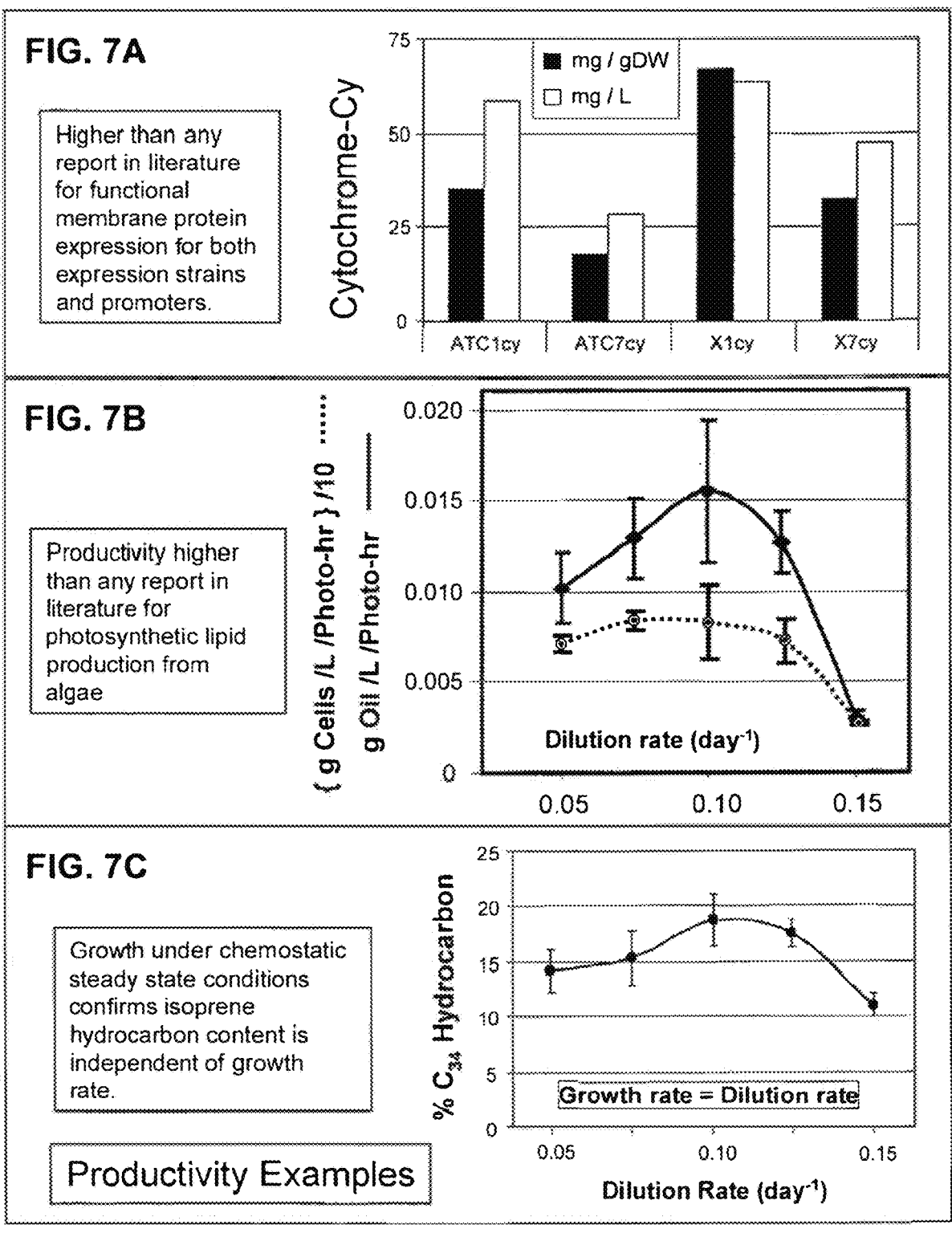

FIG. 7A

Higher than any report in literature for functional membrane protein expression for both expression strains and promoters.

FIG. 7B

Productivity higher than any report in literature for photosynthetic lipid production from algae

FIG. 7C

Growth under chemostatic steady state conditions confirms isoprene hydrocarbon content is independent of growth rate.

Productivity Examples

High density Fed batch growth; by comparison, fed shake flask culture controls < 2 gDW/L Exponential growth of cyanobacteria in simple batch culture growth on trickle-screen.

FIG. 8C    Continuous of *Botryococcus braunii* in Trickle-photobioreactor

TRICKLE-FILM BIOREACTOR AND METHODS OF USE THEREOF

CROSS-REFERENCE TO RELATED APPLICATIONS

This application is a continuation of U.S. application Ser. No. 16/238,941, filed on Jan. 3, 2019, which is a continuation of U.S. application Ser. No. 14/729,692, filed on Jun. 3, 2015, which is a continuation of U.S. application Ser. No. 12/387,140, filed on Apr. 28, 2009, now abandoned, which claims the benefit of priority of U.S. Provisional Application No. 61/048,327, filed Apr. 28, 2008 the contents of which applications are incorporated by reference herein in their entireties and for all purposes.

STATEMENT REGARDING FEDERALLY SPONSORED RESEARCH OR DEVELOPMENT

The work in this application was not based on federally sponsored funding. The work was conducted by the inventor with assistance of undergraduates and a non-degree student who were not supported by award number 0828648 from the National Science foundation (Started Nov. 1, 2008) entitled "Development of a Sustainable Production Platform for Renewable Petroleum Based Oils in Algae" for the data presented herein.

BACKGROUND OF THE INVENTION

Field of the Invention: The present invention relates to a trickle-film photobioreactor that is useful for the growth of photo-heterotrophic anaerobes for membrane protein production, as well as for the growth of many other kinds of phototrophic organisms including but by no means limited to algae and cyanobacteria.

Description of Related Art: Sealed, enclosed turbulent thin film photobioreactors known in the art have not been known for use to culture photoheterotrophs heretofore, or any phototrophic anaerobic organisms. However, photoheterotrophic anaerobes are particularly desirable as agents for expression of membrane proteins. The ability to achieve simultaneous induction of new membrane formation during heterologous protein expression is a particularly important and unique feature of *Rhodobacter. Rhodobacter sphaeroides* (ATCC 17023) is an anaerobic photoheterotroph, and thus uses light to produce membrane potential to facilitate consuming reduced carbon substrates such as organic acids. *Rhodobacter sphaeroides* (ATCC 17023) was developed by Argonne National Laboratory for use as a membrane protein expression organism, because it is a bacterium that has an internal membrane related to photosystems and that is inducible to accept heterologous protein. Because photobioreactors for *Rhodobacter* are believed to have been unknown prior to the present invention, the competing technologies were *E. coli*, yeast (including *Pichia pastoris*) and mammalian cell culture. Notably, *E. coli* lacks intracellular membranes. Accordingly, a need remains for a photobioreactor designed to permit, and ideally to optimize, culture of *Rhodobacter* for the expression of desired membrane proteins for pharmaceutical and other applications of such proteins.

Turbulent thin film photobioreactors have also not been described for the growth of algae. There are extensive descriptions of vertical photobioreactors to achieve higher productivity per land area and better photon use, however, these utilize tubes, glass plates, transparent films, etc. to retain larger vertical liquid volumes than can be achieved based on gravity-driven flows on a vertical matrix. The current application achieves utility by overcoming the inherent limitation of gravity driven vertical flow through nutrient-balanced operational strategies for ultra-high density culture during rapid growth that have not been described in the literature.

BRIEF SUMMARY OF THE INVENTION

In order to meet this need, the present invention is an apparatus for the growth of *Rhodobacter*, particularly *Rhodobacter sphaeroides* (ATCC 17023), designed to provide good and in many cases optimal growth of the organism particularly for the expression of membrane proteins as well as cyanobacteria and algae for the production of isoprene hydrocarbons. The apparatus uses a turbulent thin film as the support matrix for a culture medium (optimally a high density culture medium) on which light exposure drives heterotrophic growth of *rhodobacter* and expression of membrane proteins. The invention likewise embraces a fed-batch method of growing *Rhodobacter*, particularly *Rhodobacter sphaeroides* (ATCC 17023), according to a protocol designed to prevent salt or other toxicity based on pH control. The chemistry of the fed-batch system is such that, in the preferred embodiment, organic acid (such as without limitation lactates, malates, acetates, succinates and or formates) plus a strong base allows *Rhodobacter*, particularly *Rhodobacter sphaeroides* (ATCC 17023) to metabolize both the acid and the base as nutrients with the respective waste product being water, which in turn prevents toxicity in the medium despite high cell concentration organism growth and high yield membrane protein expression. The apparatus has also been demonstrated as a photoreactor for other organisms including but not limited to algae and Cyanobacteria. For algae, control is achieved based on a nitrogen mass balance. The apparatus is characterized by a perforate screen or reticulated sheet down which the liquid containing the culture and nutrients may flow, which perforate screen or reticulated sheet can be enclosed in a transparent enclosure. The screen material may be literally window screen stock, although to impede downward flow of the culture liquid and to encourage its turbulent mixing, the screen orientation is optimally diagonal, rather than having the wires of the screen extending horizontally and vertically. The trickle-film material need not be a window screen type material but may alternatively be any reticulated polymer sheet or arrangement, although interstices and/or clear materials are preferred so that light not absorbed by organisms in the culture is free to pass through the screen or sheet to reflect/refract back to a different area of the culture medium.

BRIEF DESCRIPTION OF THE DRAWINGS

FIG. 1A is a schematic showing the laboratory scale apparatus of the present invention;

FIG. 1B is a schematic of a scaled up photobioreactor system with multiple trickle films and liquid distribution provided to the top of the trickle-screen;

FIG. 1C is a schematic view of an alternative field implementation utilizing a surface aerator impeller in a sump to facilitate culture redistribution to the screen;

FIG. 3A is a schematic to illustrate the design characteristic of a screen to facilitate full utilization of incident light;

FIG. 3B is a schematic to illustrate the design characteristic of a screen where fluid drag induces mixing to effectively utilize energy expended in recirculation;

FIG. 3C is a schematic to illustrate the design characteristic of a screen where directional changes in flow facilitate mixing and increase liquid holdup;

FIG. 5A presents data for fed-batch growth of *Rhodobacter sphaeroides* to high density under anaerobic photoheterotrophic conditions;

FIG. 5B is a schematic of the feed batch operational control logic used in 5A;

FIG. 7A is an example of ultra-high productivity achieved for membrane protein expression using photo-heterotrophic *Rhodobacter sphaeroides;*

FIG. 7B is an example of ultra-high productivity achieved for isoprene hydrocarbon production using photoautotrophic *Botryococcus braunii;*

FIG. 7C illustrates growth rate independent hydrocarbon production in continuous culture of *Botryococcus braunii;*

FIG. 8C demonstrates long-term continuous culture of *Botryococcus braunii* on trickle-screen and illustrates conductivity as potential simple monitoring rather than adapting correlations for optical density that change with culture aggregation.

DETAILED DESCRIPTION OF THE INVENTION

Figures 2A, 2B:
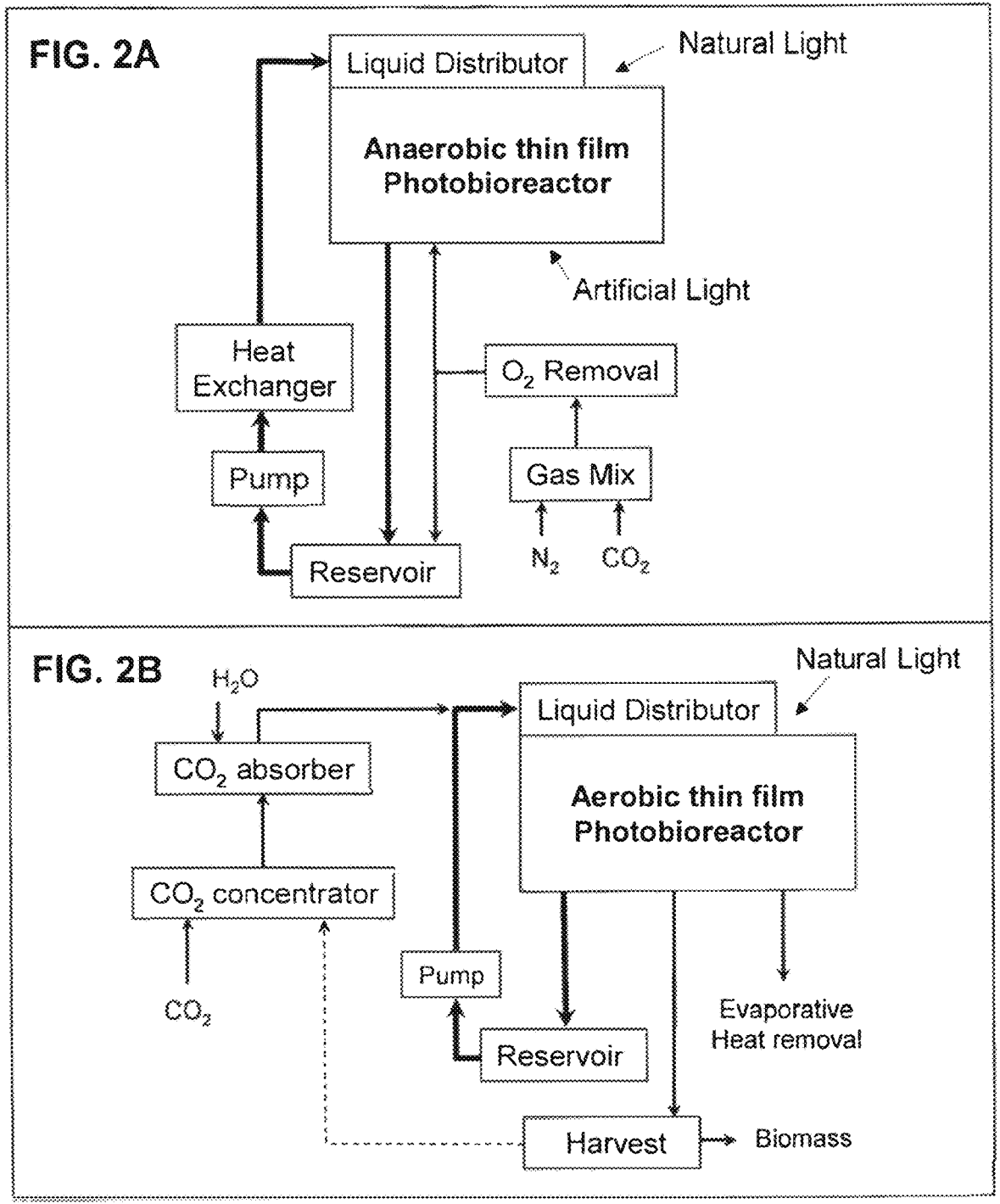
FIG. 2A is a process flow diagram for an anaerobic implementation of the photobioreactor.
FIG. 2B is a process flow diagram for an aerobic implementation of the photobioreactor that includes dissolved $CO_2$ feeding.

The present invention is an apparatus for the growth of photosynthetic organisms. The design facilitates high density growth of *Rhodobacter*, particularly *Rhodobacter sphaeroides* (ATCC 17023), for the expression of membrane proteins. The invention embraces a fed-batch method of growing *Rhodobacter*, according to a protocol designed to prevent salt or other toxicity, and utilizes pH control based on organic acid consumption. The apparatus can also be used as a bioreactor for other organisms and or application that requires efficient gas exchange and light-driven reaction; cyanobacteria are shown to display sustained exponential growth, and extremely high hydrocarbon productivity is achieved using *Botryococcus braunii*. In the implementation for *Botryococcus*, the invention embraces a stoichiometrically-balanced feed for long-term continuous culture. The laboratory scale apparatus is characterized by a clear (transparent) incubator bag or similar enclosure (FIG. 1A) containing a perforate screen, down which the liquid containing the culture and nutrients may flow. The screen material may be literally window screen stock, although to impede downward flow of the culture liquid and to encourage its turbulent mixing the screen orientation is optimally oriented on the diagonal, rather than to allow the wires of the screen to extend horizontally and vertically. The trickle-film material need not be an actual screen material, however, but may alternatively be any minimal material support for a flowing film where the liquid film is thin (<1 cm, preferably <0.5 cm, most preferably in the area of 1 mm, in thickness). Having said that, however, interstices and/or clear materials are preferred as the constituents of the screen or sheet so that any light not absorbed by organisms in the flowing culture is free to pass through the screen or sheet to reflect back to a different area of the culture medium, to be absorbed within the high cell concentration culture and not reach the underlying support. This mode of operation distinguishes this invention from similar geometries that seek to retain/immobilized an organism within the matrix and utilize a low velocity liquid perfusion to feed the retained cells. The chemistry of the fed-batch system is such that organic acid (such as without limitation lactates, malates, acetates, succinates and or formates) plus a reduced nitrogen base (such as ammonium) allows *Rhodobacter*, particularly *Rhodobacter sphaeroides* (ATCC 17023) to metabolize both the acid and the base as nutrients with the respective waste product being water, which in turn prevents toxicity in the medium despite high cell concentration organism growth and high yield membrane protein expression.

The laboratory scale apparatus provides a down-scaled model for large scale implementation. The liquid may either be pumped onto the screen via a liquid distributor at the top of the screen (FIG. 1B) or alternatively pumped using a surface impeller to create a spray that would minimize unproductive dark culture conditions in pipes and vastly simplify the cost of field installation (FIG. 1C). Such surface impellers have been developed for use in the waste-water treatment industry for oxygen aeration, and will need to be modified to provide uniform spray of culture throughout a given 'process cubical'. Algae and product will be harvested from the outlet flow that will preferably be facilitated by gravity flow among adjacent tanks.

Anaerobic operation requires an enclosure with provisions for oxygen removal and for heat removal as the high intensities of light utilized will rapidly heat up the gas within the enclosure because there is no means for evaporative cooling (FIG. 2A). Aerobic implementation may or may not require an enclosure. An enclosure provides for gas contacting of typical flue gas composition (5-15%), but involves ground-level toxic gas distribution issues. The high evaporation rates that result from non-captured and non-photosynthetic solar radiation provide a means of delivering dissolved $CO_2$ in the evaporative make-up stream (FIG. 2B). In this configuration, handling of concentrated gasses (near 100% $CO_2/NO_x$) would be advantageous and utilize developing $CO_2$ capture technologies.

Referring now to FIG. 1A, the laboratory scale turbulent trickle-film bioreactor is shown in perspective view whereby culture medium (such as shown occupying the reservoir) passes via pump (usually a peristaltic pump) through a heat exchanger into a liquid distributor and thence onto the screen. After the culture medium travels down the screen, it travels along the bottom of the bag or bubble enclosure (shown in FIG. 1A as a rectangle) and back into the reservoir. Overall, as little as possible medium is allowed to be in the reservoir or traveling through the pump, heat exchanger and etc. at any given time—the point of the reactor is to keep as much of the culture exposed to light as possible on the trickle-film screen. In fact, as the culture medium becomes thicker and the trickle-down effect more turbulent, it is the very turbulence of the screen which keeps all of the organisms in the culture medium in contact with the light sources at least during part of their turbulent descent, as the culture medium mixes and redistributes during the trickling process.

The aforementioned turbulent redistribution may be seen in illustration in FIGS. 3A, 3B and 3C. FIG. 3A shows that due to interstices in the screen, light is able to pass through the interstices (reflection/refraction) until it contacts and is absorbed by microorganisms (represented as annular rings in FIG. 3A). FIG. 3B illustrates in side elevational view how the solid boundary drag effect—of culture medium trickling down the screen-creates mixing (the arrow shows the rotational flow within a droplet of culture medium as it trickles down) so that all the culture medium throughout the ultra-thin film can be brought into direct contact with the light source for at least some of the trickling process. Note that actual flow can be continuous rivulets; nonetheless, the illustrated drag-induced rotational mixing is experienced in these flowing films. FIG. 3C shows how screen material, oriented on the diagonal, can lengthen the trickle path and create flow impedance and momentum re-direction increase holdup and mixing of the culture medium, during use of the present bioreactor.

Figures 4A, 4B:
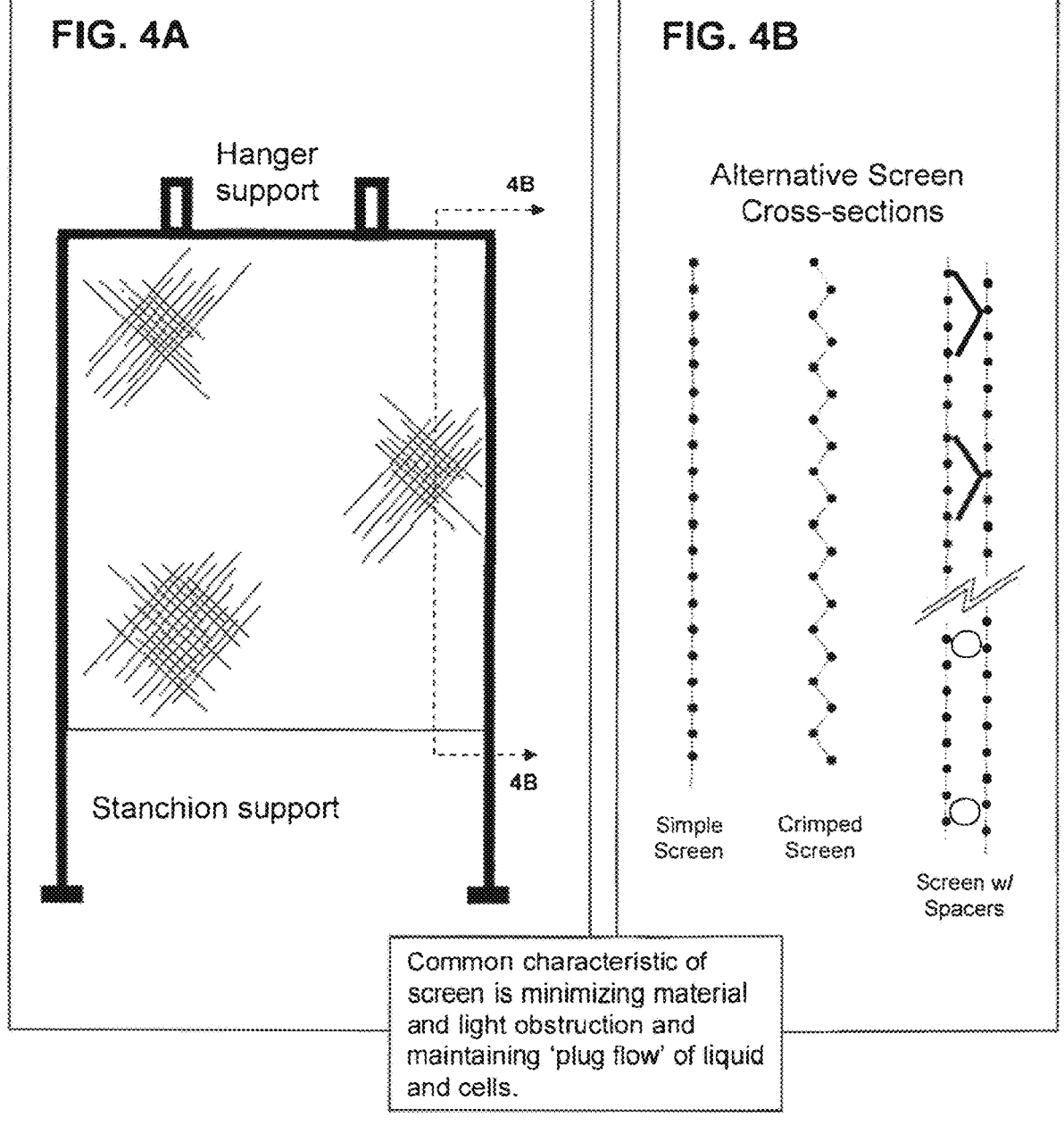
FIG. 4A is a schematic of screen supported either from above by stanchions from below.
FIG. 4B is a sectional view of 4A depicting options of screen that includes crimping or spacers while still retaining light penetration and minimizing light obstruction.

Implementation details for the screen are presented, without limitation for different configurations (FIG. 4). If liquid distribution is via plumbing to the top of the screen, then the screen would preferably be suspended from the structure supporting the liquid distributor. Spray distribution would require stanchion support. Several alternative screen implementations are presented in FIG. 4B which include crimping the screen which would induced additional tortuous flow pattern to increase mixing and increase fluid hold up analogous to the discussion of the use of a diagonal screen. By placing a spacer between two screens, liquid holdup can be increased due to an additional dimension of surface tension forces. Such a screen with spacers would also facilitate capturing of a spray. Nonetheless, the common characteristic of the design of the screen is to minimize materials and minimize light obstruction, particularly in those areas that periodically experience drainage and would otherwise become opaque to light transmission if a solid or thick fibrous material were used.

Another important characteristic of the invention is the intention to keep the photosynthetic organisms suspended in the fluid. As such, it is desirable that the flow patterns avoid channeling and back-mixing. This flow characteristic can be readily quantified by introducing a tracer and evaluating the spreading of the peak. The preferred configuration would provide flow patterns corresponding to the equivalent of 5 or more stirred tanks in series.

Prototype Construction: The prototype bioreactor construction utilized turbulent flow on window screen material with residence times of the liquid from top to bottom of only a few seconds. The surrounding plastic bag ("anaerobic turbulent film culture bubble") with liquid connections to a lower liquid reservoir, recirculation pump and liquid return to a distributor at the top of the screen (FIGS. 1-6). FIG. 5 is a perspective representation of one possible configuration of such an apparatus; an analogous apparatus is shown in schematic in FIG. 1. The bubble or bag is transparent as possible to phototrophically active radiation and made of clear film such as polyethylene copolymer or polypropylene, although any large enclosed space having clear walls suffices. A typical dimension of a clear bag can be 33.5" height and 29.5" width, heat sealed at the bottom. Prototype manufacture was conducted as follows. The bag was glued to a head plate with hot glue, and then a bead of silicone sealer was run along the top where the bag extended up beyond the head plate. Silicone sealer was also used to seal the bottom of the bag. Liquid delivery to the screen was supplied through a liquid distributor, such as a pipe having multiple perforations and able to distribute liquid onto the screen. For example, a head plate was snug-fit penetrated with $3/8$" OD ridged white PVC pipe, sealed with silicone sealer and connected above and below with 90 degree quick connect fittings (WATTS WATER TECHNOLOGIES, PL-3022). The liquid distributor was constructed in one embodiment as a tube-within-a-tube to even out flow; culture entering both ends was sprayed upward through small diameter holes and allowed to roll down to an array of larger holes drilled in a $1/8$" zig zag array along the top of the screen (trickle-film substrate). Head-plate was constructed from 0.25" thick, 8.25"×22" PLEXIGLAS acrylic (polymethyl methacrylate) to match the dimensions of the plastic bag. All drilling was completed at 600 rpm using aluminum cutting fluid to assure smooth bores. Corners were hung with stainless steel hook-eyes (#8-32), bolts and fender-washers. The bolt-nut-washer on the inside of the culture system was coated with a seal of silicone sealer. Significant bowing of this design was noted during the run and an additional central support can be a useful addition and well within the skill of the art. Large-bore, thin-wall stainless tubing was used as gas inlets and outlets to minimize problems of surface tension mediated condensate blocking of air flow.

In construction of the bag or bubble and the trickle-film insert, such as a screen or alternative, the screen may be oriented in a vertical position or may be slanted up to 45 degrees off vertical, to increase culture medium travel time and turbulence. The reservoir could be, without limitation, 1-L Aspirator Bottle with Sidearm (Corning, Corning PYREX® IL Product #1220-1L). The reservoir may, for example, sit on top of a large stir plate (Thermolyne Cimarec-3) to mix at night to prevent setting. The reservoir top may have a #6 silicone stopper, penetrated by two stainless steel gas ports (in/out as head-plate) and a fluid return ($5/16$ outer diameter (OD), $1/16$ inner diameter (ID), 12.5" in length and with a 0.45 mL dead volume) reaching to the bottom of the reservoir, for example. Sampling may be facilitated with a piece of silicone tubing ($3/16$ OD) at the end of the sample tube-generally capped and clamped between samplings. Culture media may be pumped for example from the reservoir through Neoprene tubing (such as Norton/Masterflex 6402-18) connected to Norprene® industrial grade tubing $3/8$" ID×$9/16$" OD×$3/32$" wall through the pump (both chosen to minimize oxygen diffusion). A Watson-Marlow 601S or similar peristaltic pump may be used to minimize tubing damage and to permit long-term operation with rollers adjusted to accommodate tubing wall thickness. Initially, flow can be 0.7 L/min (such as a 30% setting) which can be increased to 1-L/min during rapid growth (such as a 40% setting) until the increase in viscosity predictably requires flow adjustment back to 0.7-L/min to prevent excessive gas aspiration. Other similar operating parameters are likewise typical.

The feed materials and stoichiometry of the fed-batch system are described in Appendices B and C attached hereto.

The following Examples are illustrative.

EXAMPLE 1: *Rhodobacter sphaeroides* anaerobic growth and membrane protein production. *Rhodoabcter sphaeroides* (strain ATCC 17023) was grown under anaerobic photo-heterotrophic conditions with fed-batch operation. A formulation for a defined media MR26 (see Appendix A) was provided by personnel at Argonne National Laboratory. Inoculum was grown for a week with 25% media replacement daily in a sealed media bottle to adapt to high light conditions (>500 $\mu E/m^2/s$). The shake flask control was half of the 1-L inoculum grown on a NEW BRUNSWICK G10 gyratory shaker (120-rpm, 1" STROKE). Sampling was conducted 4 times per day including midnight and 8 am to assess biomass loss during the night due to respiration; this high-frequency sampling was assessed with $OD_{660}$ because it utilized very small culture samples. Using the bioreactor described in detail in the foregoing portions of this patent application, the following growth conditions were observed using the culture thus prepared. Cultures were grown in a CONVIRON incubator with a 16-hr photoperiod. Room lighting provided 1000 $\mu E/m^2/s$ during most of the day from 1 bank of high pressure sodium vapor, and 3 banks of metal halide lamps. Lighting was ramped up during 1-hr in the morning and 1-hr at midnight. When the culture started to display rapid growth, supplemental near-UV light was provided by (2) 40-watt actinic black lights (no dark glass filter; PHILLIPSF40T12/BL) and subsequently with a 500-watt halogen work light (set of 3-ft distance) to provide additional far red lighting. The temperature of the room was 28° C. during 9 am-11 pm and ramped to 25° C. at night. Temperature was monitored inside the reactor and shake flask control once a day by flowing a 4-mL sample over a digital temperature probe as it was collected into a screw-cap test tube. The bioreactor culture was passed through a heat exchanger to help to manage heat and minimize evaporative water. This heat exchanger consisted of a 24" long piece of ⅜" OD thin wall stainless steel tubing that passed through a set of (3) 1.5" TRI-CLOVER sanitary stainless steel Long-Tees (tube diameter approximately 1"). Culture flowed through the central pipe that was sealed to the sanitary fittings with silicone rubber stoppers and connected to a pump and a fluid distributor on a head place with quick-connect fittings, with tubing for cooling was provided there-around. Cooling water was recirculated through a refrigerated circulating bath (FISHER ISOTOPE, Model #89100) that was adjusted to between 28-29° C. to minimize evaporative water loss in the system.

An anaerobic environment was provided inside the culture system by providing a 10% $CO_2$, 90% nitrogen gas supply that was scrubbed for oxygen removal. Gas was mixed using BROOKS 1355 SHO-RATE "150" flow meters for carbon dioxide and nitrogen. Gases were delivered via vinyl tubing: residual oxygen removal was facilitated by 3-L of 11.7 g. sodium sulfite catalyzed by 2.3 mM $Co^{2+}$ (1.7 mg. $CoCl_2$-$6H_2O$). The cobalt level was chosen to be twice the recommended level for measuring gas-liquid interface mass-transfer coefficients to provide for the interface-enhanced reaction rates for oxygen removal. An additional 17.6 g. $Na_2SO_3$ was added to the humidification column on day 2 along with 250 UL 0.1% resazurin oxygen indicator to assure excess oxygen removal capacity. Gas then passed from the reactor to a manifold that provided for inlets to the shaker-flask control as well as to the inlet of the reservoir bottle and the bag head-plate. A gas connection to the head-plate gas exit from the reservoir was also provided to provide for gas equilibrium in anticipation that the liquid pumping and draining flows would provide for very complex requirements of gas flow to avoid flooding and/or bursting of the bag.

Growth assessment was conducted as follows. Optical density was measured at 660 nm ($OD_{660}$) corresponding to the minimum in spectral absorbance for *Rhodobacter sphaeroides* using a MILTON ROY SPECTRONIC 20D with infrared phototube and filters. This approach avoids potential influence of alteration of cell pigment content on the correlation between optical density and dry weight. Dry weights were determined by taking 6-mL. of culture and centrifuging at 2851-rcf (35000 rpm) for ten minutes at 4° C. Initial supernatant was sampled for a media sample followed by addition of an aliquot of distilled water, resuspension and centrifugation again. The pellet was rinsed and the biomass recovered by means known in the art. Viable cell number was assessed by dilution plating on YCC media and placing plates upside down in an incubator (not the present apparatus) under translucent plastic containers to provide light of about 100 $\mu E/m^2/s$. Under these conditions it was observed that *Rhodobacter* colonies would initially develop unpigmented, then turn a deep red-brown color to provide validation that colonies were not contaminants.

Culture rheology was measured as follows. Viscosity measurements were carried out on a BROOKFIELD ENGINEERING DV-III (V3.3 LV) cone & plate rheometer interfaced to a computer using a CPE-51 spindle. Viscometer was calibrated with precisely prepared sucrose solutions at 0.211, 0.498, 0.711, 1.012 and 1.207-g sucrose per gram of water with corresponding literature values of viscosity thereof.

The results of the above described experiment were as follows. Two initial days of very limited growth demonstrated that the cultures were severely carbon limited in MR26 media. Subsequently, a fed-batch approach to providing nutrients was devised (see Appendices B and C). Biomass accumulation as measured by $OD_{660}$ is shown in FIG. 7 (which shows a decline each night, and down-spikes that correspond to media additions). Because the volumes in the cultures were kept within 10% of the initial volume, the growth trends shown are valid. In FIG. 7 the dashed lines represent the feed of carbon as succinate to the system. Since the succinate level in MR26 media corresponds roughly to an $OD_{660}$ of 1, the use of increments of MR26 media as the index of feeding provides a good visual assessment of excess availability of succinate throughout the culture for both the bioreactor and the shake flask control.

Figures 8A, 8B:
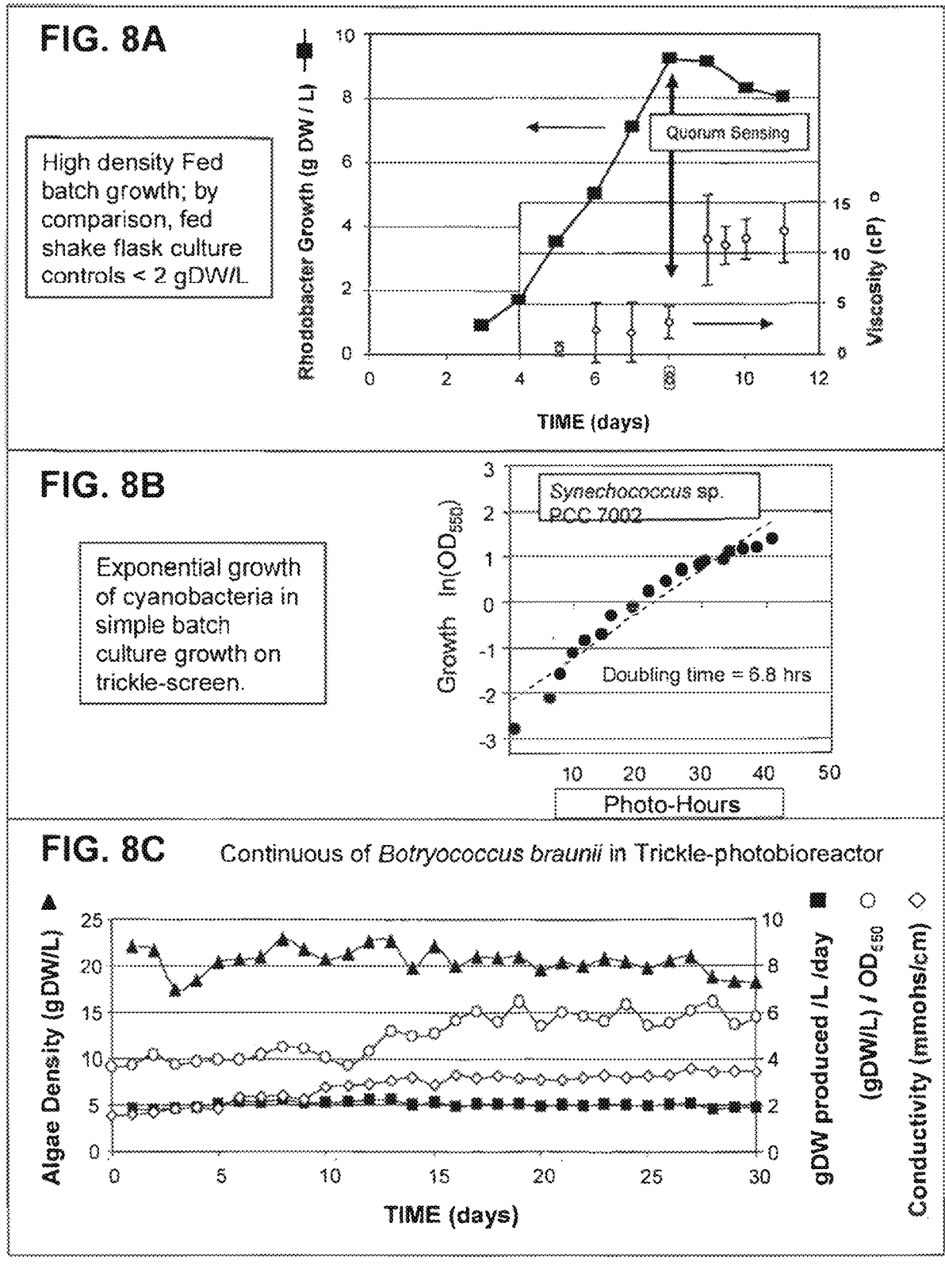
FIG. 8A demonstrates high productivity anaerobic photoheterotrophic growth conditions that appear to be limited by quorum sensing in *Rhodobacter sphaeroides* (insert)
FIG. 8B demonstrates exponential growth of a cyanobacterium over nearly 4 decades of increased cell number during growth on trickle screen.
Figure 9:
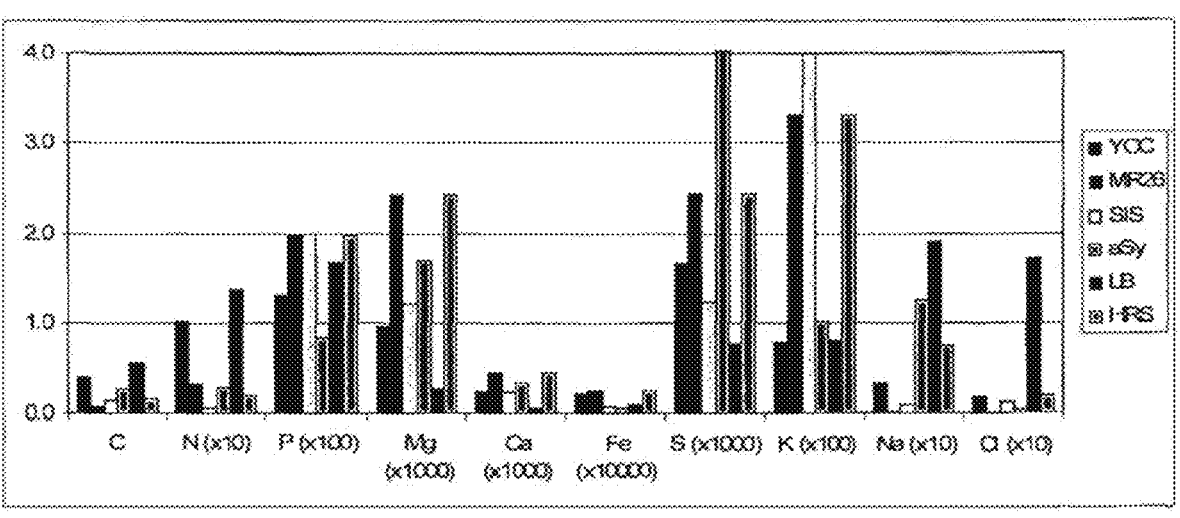
FIG. 9 plots composition of various media (including stoichiometrically evaluated complex media) that have been used to support growth of *Rhodobacter.*

FIG. 8 provides a tracking of the C/N and C/P ratios that were used throughout the feed strategy, to work towards a final total media composition that more closely matches the nutrient composition of the biomass. Biomass accumulation was assessed each night by centrifugation and freeze-drying. FIG. 9 shows the accumulation of dry weight that is quite linear after the feed strategy was implemented to avoid succinate limitation. By comparison, prior art techniques typically achieved cell densities of only 1.3 gDW/L during studies of light-limiting growth and hydrogen production using media containing yeast extract, and the unaltered MR26 defined medium used in this work itself supports only about 0.5 gDW/L.

Dilution plating revealed only three contaminant colonies among the 2000 colonies observed, indicating that rather good asepsis was maintained despite minimal sterilization and aseptic procedures. This good asepsis is attributed to the use of a defined medium (no extracts or hydrolysates) and succinic acid as the carbon source, which few organisms can utilize as a carbon source under anaerobic conditions. Plots of colony forming units (CFU) show that cell concentrations at inoculation were roughly $2 \times 10^9$ cells per mL, and increased by a factor of 10-fold during growth in the reactor. This high cell concentration at inoculation was facilitated by the week-long adaptation of the inoculum under the high light conditions of the CONVIRON incubator.

On day 8, there was a dramatic change in culture behavior. There was extensive foaming, and the culture flow through the system was clearly more viscous. The addition of anti-foam (0.1 mL 0.02% by volume SIGMA Antifoam 289) completely eliminated foaming and caused a dramatic improvement in spreading of the culture on the screen. After day eight, the culture would seem to grow during the day, but would lose the majority of the increase in $OD_{660}$ overnight until morning. The culture seemed extremely viscous and difficult to pipette for dilution plating and optical density measurements. The viscosity of the supernatant was measured as shown in FIG. 8A, showing that viscosity increased to greater than 10 centipoise at precisely the time when growth ceased. Insignificant difference in supernatant viscosity was observed when treated with DNAse, demonstrating that this viscosity increase was not due to cell rupture and release of DNA to the media. In frozen samples, the medium was observed to form a semi-solid gelatin, which could be warmed and "melted" giving the same viscosity measurements with or without freezing. It is speculated that this viscosity results from the secretion of polysaccharides and possibly mediated by quorum sensing, and therefore it is concluded that much higher cell concentrations could be achieved for organisms or strains which do not display this behavior.

An assessment of productivity of *Rhodobacter sphaeroides* for membrane protein expression was undertaken using genetically engineered strains expressing a C-type cytochrome from *R. capsulatus* in *R. sphaeroides* developed at Argonne National Labs [Laible et al., 2008]. This expression included both wild-type (ATCi) background strains and a chromosomal knockout for the light harvesting II {LH2-} complex (Xi). Cultures including using constructs based on the puf operon driven by the LH1 promoter in wild-type and {LH2-} chromosomal knockout (ATC1, X1), and the puc operon driven by LH2 promoter in the same strains (ATC7, X7). Quantification of cytochrome-Cy is measured using a immunodetection procedure for gel analysis (poly-his antibodies) that avoids problems of staining and aggregation-dependent gel mobility with membrane proteins [Laible et al., 2008]. Blots were exposed at different levels by 'gray shielding' with a sandwich of film using MAJIC MARK/PROSIEVE MW standards. The positive control is a whole cell lysate from a *Rhodobacter* strain expressing reaction centers at 1 mg/L (his-tag on C-terminus of M chain of ~28 kD) and the negative control is from a *Rhodobacter* strain carrying an empty expression plasmid. The results shown in FIG. 7A represent what appears to be the highest ever recorded expression level for functional membrane proteins. When these expression levels in excess of 50 mg protein/g DW are combined with the fed-batch bioreactor runs noted above (FIGS. 5A & 8A), the *Rhodobacter* expression platform implemented in the disclosed invention has the potential to achieve hundreds of milligrams of functional membrane protein per L. This is several orders of magnitude higher than other expression hosts [Sarramegna et al., 2003].

EXAMPLE 2: As a simple demonstration of photosynthetic growth, one of the reportedly fastest growing Cyanobacteria (Synechocccus sp PCC 7002) was obtained and grown on a modified Bold's media formulation. This culture displayed an extended exponential growth with a doubling time of just under 7 hours (FIG. 8B). Since this medium did not support growth to ultra-high densities, an extensive evaluation of algae growth media was undertaken to identify a media that would be stoichiometrically balanced. In addition to examining algae media (Bolds, HS) the media formulations for plant tissue culture (MS and B5 media) were also compiled for comparison because these media were developed based on plant biomass elemental composition and have been shown to successfully support high density culture. The resulting medium is given appendix B and is the basis of subsequent high density algal culture work.

EXAMPLE 3: Growth of *Botryococcus braunii* in continuous flow trickle film culture for the production of hydrocarbons. Dilute algae cultures will photobleach and die if exposed suddenly to high light conditions. Similarly, the amount of nutrients needed to support ultra-high density algae culture would be toxic if all were added at the beginning of culture. However, if cell density is increased with fed-batch culture and then media is removed and replaced at a frequent (even daily) basis, the cells will self-shade and not be exposed to the high concentration nutrients as they are diluted into a culture that is rapidly consuming the inorganics. This operational condition is what would be encountered in an industrial setting. This final example describes the growth of the hydrocarbon-producing strain of *Botryococcus braunii* strain B that produces $C_{34}$ isoprene hydrocarbons in an extracellular matrix [Metzger et al., 1985].

Initial experimentation was carried out to develop the operational strategy where correlations for dry weight based would be used to replace the nitrogen that was consumed on each culture interval. The operational strategy is outlined in FIG. 6B where optical density is measured at 550-nm $(OD_{550})$ to avoid interference with chlorophyll and provide a correlation to dry weight. Since *Botryococcus* was observed to aggregate differently at different growth rates, the correlation between $OD_{550}$ and dry weight needed to be updated with experimental measurements. Since dry weight measurements take several days to obtain, the daily media addition was estimated based on the observed change in growth as correlated to dry weight. A nitrogen mass balance then provided the basis for concentrated nutrient replenishment. Since *Botryococcus* floats, dry weight determination required freeze-drying samples in pre-tarred Epi-tubes and the weight of the media was determined by subtraction of the freeze-dried weight of a micro-filtered media sample of the same culture.

Figure 6A:
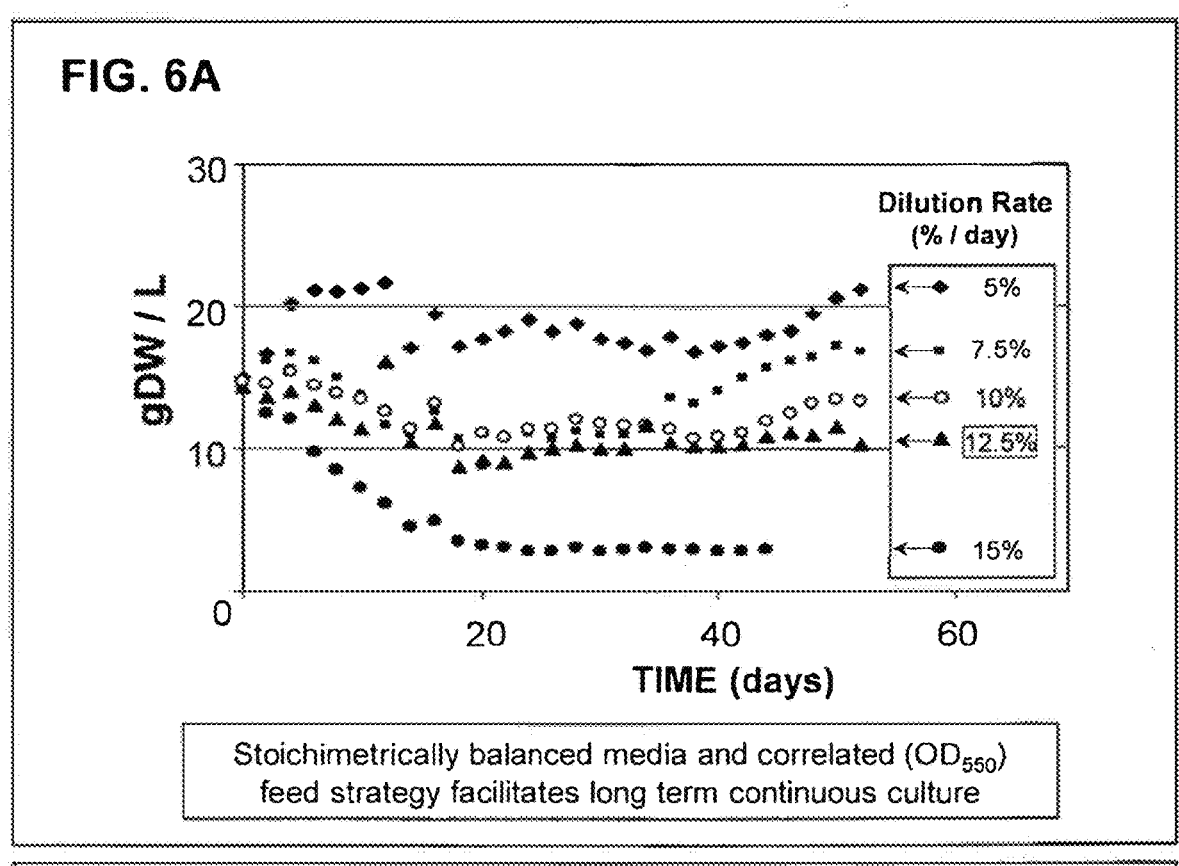
FIG. 6A presents data for continuous culture operation for *Botryococcus braunii;*
Figure 6B:
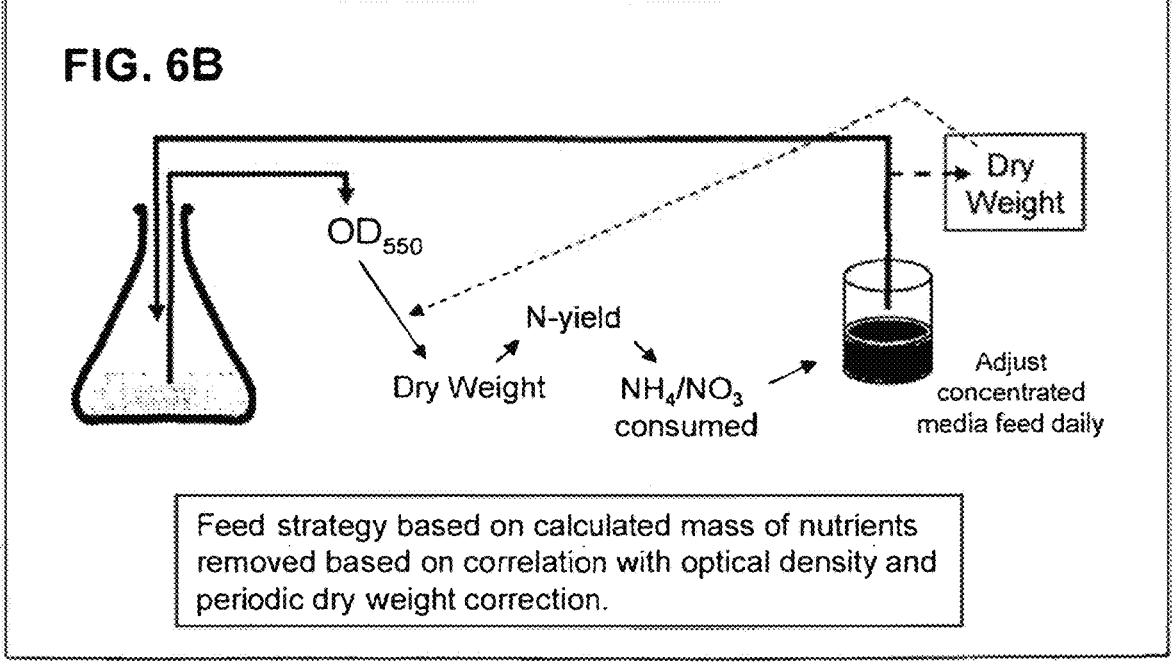
FIG. 6B is a schematic of the stoichiometrically rationalized nutrient feeding strategy used in 6A.

FIG. 6A show growth kinetics of such a continuous cultures operating under light-limited (~300 E/m²/sec; 16:8 hours light/dark cycle) conditions at various dilution rates. Experiments were conducted in shake flasks, maintained with ~5% $CO_2$ in headspace of a 500 mL Erlenmeyer Flask containing 50 mL culture. $CO_2$ delivery was facilitated by mixing compressed air and pure $CO_2$ using volumetric flow meters and silicone tubing. $CO_2$ was shut off at night by utilizing a solenoid connected to a 24-hr cycle timer. Flasks were setup in a daisy chain fashion with a gas flow rate of 100 mL/min. Aseptic technique was used to maintain monoculture of *B. braunii*. The flasks were grown on a gyratory shaker at 122 rpm. In this manner, the sampled steady state cell concentration eventually stabilized and was observed to be linearly dependent on dilution rate consistent with light-limited growth (FIG. 6A). The resulting algae biomass productivity of 0.08 g DW cells per liter per photo-hour is as very high as a result of achieving light limiting growth rate despite the slow growth rate of this algae species (doubling time 4-5 days). Hexane extracts were analyzed for botryococcenes to reveal that the high density steady state operational condition achieved an oil production rate higher than any other previous report (0.015 0.015 g oil/L/photo-hr; FIG. 7B).

In a chemostat, the dilution rate is equal to the growth rate and this is valid for this rapid semi-continuous operation described in this disclosure. The production of oils was found to be independent of the growth rate (FIG. 7C) so that high productivity is achieved at high culture growth rates. The foregoing bioreactor was used for operating a continuous culture of *Botryococcus braunii*, race B under light-limited conditions for 1 month, utilizing the operational strategy described in FIG. 6B, and a dilution rate of 7.5% (16:8 hours light: dark cycle; ~600 µE/m$^2$/sec). Volume of culture was maintained at 500-mL and media replacement was carried out once a day. FIG. 8C displays growth kinetics where a productivity of roughly 2 gDW/L/day was obtained and a correlation was observed between dry weight and conductivity to provide an alternative means of monitoring growth that would not be dependent on aggregation of cells. These examples show that the trickle-film photobioreactor productivity is capable of achieving the highest biomass and oil for photosynthetic production of hydrocarbons and tryiglycerides.

Although the invention has been described above with particular reference to a several specific examples, and to specific materials and methods, the invention is only to be considered to be limited insofar as is set forth in the accompanying claims.

REFERENCES

Gamborg O L, Miller R A, Ojima K. (1968) Nutrient requirements of suspension cultures of soybean root cells. Experimental Cell Research 50:151-158.

Laible P D, Mielke D L, Hanson D K (2008). The Purple Phototrophic Bacteria. Series: Advances in Photosynthesis and Respiration, Vol. 28 Hunter, C. N.; Daldal, F.; Thurnauer, M. C.; Beatty, J.Th. (Eds.) ISBN: 978-1-4020-8814-8; In press, Available: Nov. 3, 2008

Metzger P, Berkaloff C, Casadevall E, Coute A. (1985) Alkadiene-producing and botryococcene-producing races of wild strains of *botryococcus-braunii*. Phytochem 24:2305-2312.

Murashige T, Skoog F (1962) A revised medium for rapid growth and bio assays with tobacco tissue cultures. Physiologia *Plantarum* 15:473-497.

Sarramegna V, Talmont F, Demange P, Milon A (2003) Heterologous expression of G-protein-coupled receptors: comparison of expression systems from the standpoint of large-scale production and purification. Cellular and Molecular Life Sciences, 60:1529-1546.

Appendix A

APPENDIX A

| *Rhodobacter sphaeroides* Medium (MR26+) - defined/refined media | | | | | |
|---|---|---|---|---|---|
| | MW | [final] | [stock] | prep/L | /250 mL |
| Ammonium Succinate Solution | | | | 20 mL | 5 mL |
| Succinic acid (free) | 118.09 | 1.83 | 91.5 g/L | | |
| Ammonium Hydroxide | 35.05 | | 104.5 mL/L | | |
| (NH$_4$OH) | | | (~14.9N) | | |
| (in liquid form) | | | | | |
| pH to 6.8 (in~500 mL) with NH$_4$OH | | | | | |
| Ammonium Succinate | 152.15 | 235 g/L | -na- | 2.36 g | 0.59 g |
| The following generates additional NaCl | | | | | |
| | | | | | |
| Na$_2$-succinate (Na$_2$C$_4$H$_4$O$_4$-6H$_2$O) | 270.1 | 4.19 | -na- | 4.19 | 1.05 |
| Nh$_4$Cl | 53.49 | 1.66 | -na- | 1.66 | 0.415 |
| MR26 Phosphates (50×, 1M) (pH 6.8) 1M | | | | 20 mL | 5 mL |
| K$_2$HPO$_4$ (dibasic) | 174.18 | 2.3 g/L | 115 g/L | | |
| KH$_2$PO$_4$ (monobasic) | 136.09 | 0.898 g/L | 44.9 g/L | | |
| pH to 6.8 with KOH or H$_3$PO$_4$ | | | | | |
| MR26 MICROnutrients (1000×) | | | g/L stock | 1 mL | 0.25 mL |
| ZnSO$_4$•7H$_2$0 | 287.56 | 0.0109 | 10.9 | | |
| ZnSO4•H$_2$0 | 179 | 0.00679 | 6.79 | | |
| ZnSO$_4$ (anhydrous) | 161.47 | 0.00612 | 6.12 | | |
| MnCl$_2$•4H$_2$0 | 197.41 | 0.0013 | 1.3 | | |
| CuSO$_4$•5H$_2$0 | 249.7 | 0.000392 | 0.392 | | |
| CoCl$_2$•6H$_2$0 | 237.93 | 0.0002 | 0.200 | | |
| (NH$_4$)$_6$Mo$_7$O$_{24}$•4H$_2$0 | 1235.86 | 0.000186 | 0.186 | | |
| H$_3$BO$_3$ (boric acid) | 61.83 | 0.000114 | 0.114 | | |
| Fe-EDTA•2H$_2$0 [(F)] | 403.1 | 0.0101 | 4.0 g/L | 2.5 mL | 0.625 mL |
| | | | (4 mg/mL) | | |
| After autoclaving add Mg, Ca, and vitamins aseptically | | | | | |
| | | | | | |
| Magnesium Solution (2M, filter sterilized) | | | g/50 mL stock | 1.205 mL | 0.301 mL |
| MgSO$_4$•7H$_2$0 | 246.5 | 0.596 | 24.65 | | |
| MgSO$_4$ (anhydrous) | 120.0 | 0.29 | 12.0 | | |
| Calcium Solution (1M, filter sterilized) | | | g/50 mL stock | 0.45 mL | 01125 mL |
| CaCl$_2$•2H$_2$0 | 147 | 0.0662 | 7.5 | | |
| CaCl$_2$ (anhydrous) | 111 | 0.050 | 5.66 | | |
| Vitamin Stock (1000×) Filter sterilized, 4° C. | | | g/100 ml stock | 1 mL | 0.25 mL |
| Nicotinic acid | | 3.0 mg/L | 0.3 | | |
| Nicotinamide ~~ | | 3.0 mg/L | 0.3 | | |

APPENDIX A-continued

| | | | | | |
|---|---|---|---|---|---|
| *Rhodobacter sphaeroides* Medium (MR26+) - defined/refined media | | | | | |
| | MW | [final] | [stock] | prep/L | /250 mL |
| Thiamine-HCl | | 6.0 mg/L | 0.6 | | |
| Biotin | | 0.12 | 0.012 | | |

NOTES:

⌢⌢ Nicotimamide not in SIS media; Adaptation of MR26 to reflect Macro/Micro media formulations and use the Fe-EDTA typical of other media of the lab as well as the filter sterilized Ca and Mg solutions of M9 bacterial media.

Appendix B

APPENDIX B

| | | | | | |
|---|---|---|---|---|---|
| *Botryococcus braunii* Medium (WFAM/3g-s-c) | | | | | |
| | MW | [final] | [stock] | prep/L | /250 mL |
| $KNO_3$ | 101.11 | — | -na- | 0.60 | 0.15 |
| $NH_4NO_3$ | 80.04 | — | -na- | 0.61 | 0.153 |
| MR26 Phosphates (50×, 1M) (pH 6.8) 1M | | | | 1 mL | 0.25 mL |
| $K_2HPO_4$ (dibasic) | 174.18 | 0.115 g/L | 115 g/L | | |
| $KH_2PO_4$ (monobasic) | 136.09 | 0.045 g/L | 44.9 g/L | | |
| pH to 6.8 with KOH or $H_3PO_4$ | | | | | |
| WFAM MICROnutrients (1000×) | | $1/1000^{th}$ or mg/L | g/L stock | 1 mL | 0.25 mL |
| $H_3BO_3$ (boric acid) | 61.83 | | 1.86 | | |
| $MnCl_2 \bullet 4H_2O$ | 197.41 | | 0.54 | | |
| $ZnSO_4 \bullet 7H_2O$ | 287.56 | | 0.066 | | |
| $ZnSO_4 \bullet H_2O$ | 179 | | 0.0411 | | |
| $ZnSO_4$ (anhydrous) | 161.47 | | 0.0371 | | |
| $Na_2MoO_4\text{-}2H_2O$ | 241.95 | | 0.031 | | |
| $(NH_4)6Mo_7O_{24} \bullet 4H_2O$ | 1235.86 | | 0.0229 | | |
| $CoCl_2 \bullet 6H_2O$ | 237.93 | | 0.030 | | |
| $CuSO_4 \bullet 5H_2O$ | 249.7 | | 0.0075 | | |
| $Fe\text{-}EDTA \bullet 2H_2O$ $^{(F)}$ | 403.1 | 0.0024 g/L | 4.0 g/L (4 mg/mL) | 6 mL | 1.5 mL |
| After autoclaving add Mg, Ca, and vitamins aseptically | | | | | |
| Magnesium Solution (1M, filter sterilized) | | | g/50 mL stock | 1 mL | 0.25 mL |
| $MgSO_4 \bullet 7H_2O$ | 246.5 | 0.121 g/L | 6.03 | | |
| $MgSO_4$ (anhyd ous) | 120.0 | 0.0588 | 2.94 | | |
| $MgCl_2$ | 95.21 | 0.0486 g/L | 2.43 | | |
| Calcium Solution (1M, filter sterilized) | | | g/50 mL stock | 0.88 mL | 0.22 mL |
| $CaCl_2 \bullet 2H_2O$ | 147 | 0.132 g/L | 7.5 | | |
| $CaCl_2$ (anhydrous) | 111 | 0.100 | 5.66 | | |

Appendix C: *Rhodobacter* Nutrient Feed Implementation

Summary: In addition to stoichiometric requirements for nitrogen and carbon, it is desirable to utilize an organic acid as a carbon source to prevent contamination and provide a unique selection pressure for *Rhodobacter* growth based on photosynthetic production of ATP under anaerobic conditions (Photo-heterotrophic growth with no oxygen production).

Stoichiometric requirements: The composition of various media (including stoichiometrically evaluated complex media) that have been used to support growth of *Rhodobacter* was summarized as evaluation of flexibility in nutrient levels at any given time.

Implementation: In the absence of computer control and online instrumentation, the nutrient feed strategy was imple-mented by setting up a spreadsheet to track total C,N,P added throughout the run. Carbon needs estimated based on anticipated growth till the next sample period were added as succinate along with sufficient ammonium succinate to keep nitrogen in excess but below the initial stoichiometry of ammonium succinate. Phosphate content (C/P ratio) was used as index to periodically include micro and macro nutrient solutions.

*E. coli* Glucose Utilization: Initial pH is achieved using ammonium salt (or amino-acid) which results in drop in pH during carbon consumption which is compensated by addition of base (e.g. NaOH).

$$C_6H_{12}O_6 + NH_4 + (O_2) \rightarrow \alpha CN_{0.14}O_x \ldots (NH_3\text{---R}) + CO_2/H_2O + \ldots + H^+$$

*Rhodobacter* Organic Acid Carbon Utilization: Use of an organic acid carbon source provides the opportunity to achieve the initial pH by balancing as an ammonium salt.

$$RCOOH+NH_4+(O_2) \rightarrow \beta CN_{0.14}O_x \ldots +CO_2/H_2O+ \ldots$$

However, this causes a stoichiometric imbalance;

Molar composition on carbon basis:

Biomass roughly=$CN_{0.15}$

Yeast Extract Molecular Formula=$CN_{0.29} O_{0.52} P_{0.035} H_{1.8}$

Ammonium succinate=$CN_{0.5}OH_3$

Although the use of salts (sodium succinate) could be used to correct the stoichiometry for biomass need, this results in excess salt accumulation for high cell concentration culture due to the need for high levels of nutrients.

High Density Fed-Batch Strategy: Maintain culture with stoichiometric excess nitrogen using ammonium salt of organic acid. Carbon consumption results in an increase in pH where the organic acid can be fed as the pH control agent. Carbon yield calculations allow for estimating nitrogen needs for periodic feed of ammonium salt.

What is claimed:

1. A flowing thin film photobioreactor system, comprising:

(i) an enclosure and within the enclosure, a trickle-film insert comprising one or more perforate screens or reticulated sheets oriented vertically to 45 degrees from vertical;

(ii) a light source emitting light into the enclosure;

(iii) a reservoir for collecting culture medium from the enclosure; and (iv) a means for delivering culture medium from the reservoir onto the trickle film insert within the enclosure, wherein the culture medium comprises a suspended photosynthetic microorganism, wherein the means (iv) comprises a surface impeller that sprays culture medium onto the trickle-film insert.

2. The photobioreactor system of claim 1, wherein the means (iv) comprises a pump having an inlet connect to an outlet on the reservoir and an outlet connected to a liquid distributor configured to pump the culture medium onto the trickle-film insert.

3. The photobioreactor system of claim 1, wherein the enclosure is configured to provide an aerobic environment within, the system further comprising a gas supply, meter, and tubing for delivering dissolved carbon dioxide in a makeup stream to the culture medium.

4. The photobioreactor system of claim 1, wherein the light source is located outside of the enclosure.

5. The photobioreactor system of claim 4, wherein the enclosure is transparent.

6. The photobioreactor system of claim 1, wherein the perforate screen comprises wires oriented on a diagonal.

7. The photobioreactor system of claim 1, wherein the light source emits artificial light.

8. The photobioreactor system of claim 1, wherein the perforate screen comprises a screen material.

9. The photobioreactor system of claim 8, wherein the screen material comprises wire mesh.

10. The photobioreactor system of claim 9, wherein the wire mesh is oriented diagonally.

11. The photobioreactor system of claim 8, wherein the screen material is crimped.

12. The photobioreactor system of claim 1, wherein the trickle film insert comprises two or more parallel perforate screens spaced 10 mm or less apart.

13. The photobioreactor system of claim 10, wherein the trickle film insert comprises two or more parallel perforate screens spaced 10 mm or less apart.

14. The photobioreactor system of claim 13, wherein the screens are spaced 5 mm or less apart.

15. The photobioreactor system of claim 14, wherein the screens are spaced 1 mm or less apart.

16. A flowing thin film photobioreactor system, comprising:

(i) an enclosure and within the enclosure, a trickle-film insert comprising one or more perforate screens or reticulated sheets oriented vertically to 45 degrees from vertical;

(ii) a light source emitting light into the enclosure;

(iii) a reservoir for collecting culture medium from the enclosure; and (iv) a means for delivering culture medium from the reservoir onto the trickle film insert within the enclosure, wherein the culture medium comprises a suspended photosynthetic microorganism, wherein the enclosure is configured to provide an anaerobic environment within the enclosure, the system further comprising a means for removing oxygen from the anaerobic environment, and a means for removing heat from the system.

17. The photobioreactor system of claim 16, wherein the enclosure comprises a sealed bag.

* * * * *